United States Patent [19]

Rozencwaig et al.

[11] Patent Number: 5,081,129

[45] Date of Patent: Jan. 14, 1992

[54] METHOD OF TREATMENT OF ANEMIA WITH SERATONIN ANTAGONISTS

[76] Inventors: Roman Rozencwaig, 6232 MacDonald, Hampstead, Montreal, Quebec, Canada, H3X 2X2; Bernard Grad, 5317 Snowdon, Montreal, Quebec, Canada, H3X 1Y3

[21] Appl. No.: 579,976

[22] Filed: Sep. 10, 1990

[51] Int. Cl.$^5$ ............................................. A61K 31/445
[52] U.S. Cl. .................................................... 514/325
[58] Field of Search ........................................ 514/325

[56] References Cited

U.S. PATENT DOCUMENTS 4,771,056  9/1988  Rozencwaig ........................ 514/325

*Primary Examiner*—Stanley J. Friedman
*Attorney, Agent, or Firm*—Foley & Lardner

[57] ABSTRACT

Treatment of patients suffering from anemias such as anemias of chronic disorders or anemias resulting as toxic side effects of drugs, ionizing radiation or kidney dialysis by administration of a serotonin antagonist, such as cyproheptadine, the administration taking place once a day during the evening, preferably after sunset.

7 Claims, No Drawings

METHOD OF TREATMENT OF ANEMIA WITH SERATONIN ANTAGONISTS

BACKGROUND OF INVENTION (a) Field of the Invention

This invention relates to a method for the treatment of the anemia of chronic disorders as well as those anemias arising consequent to treatment with ionising radiation or drugs or surgery or other physical procedures which may have toxic side effects such as dialysis for kidney disease. More particularly, the present invention relates to the use of cyproheptadine and other serotonin antagonists as an active ingredient for the manufacture of a medicament and the use of pharmaceutical compositions containing cyproheptadine and other serotonin antagonists for treating anemia in general and particularly for reducing the extent of the anemia of chronic disorders in patients suffering from various types of cancers, acquired immunodeficiency syndrome, kidney disease and other chronic diseases whether the anemia is due to the chronic disorder itself or the result of an applied treatment which in addition to its significant therapeutic effects may also have toxic side effects. In such instances, treatment with the serotonin antagonists would allow the continuance of the original treatment of the disease without interruption.

(b) Description of Prior Art

Anemia in a living organism broadly results from a condition in which the blood is deficient in hemoglobin or in red blood cells. Some anemias are treatable but for others effective treatment is still non-existent. Anemia of chronic disorder and toxic anemias are of that type and are found mostly in patients who suffer from neoplastic, infectious or inflammatory diseases. There is therefore a need for a cure or alleviation of these anemias.

In U.S. Pat. No. 4,771,056 issued in Sept. 13, 1988 to Roman Rozencwaig, there is disclosed a method of treating patients suffering from cancer, acquired immunodeficiency syndrome, multiple sclerosis by administration of a serotonin antagonist such as cyproheptadine. In these cases, the serotonin antagonist was found to be responsible for curing or at least alleviating the disease itself. In many cases, anemias, in particular anemias of chronic disorders are associated with chronic diseases, and there is an urgent need to find a cure or at least a treatment for such anemias since they may cause a deterioration of the patients with whom they are associated.

It is an object of the present invention to provide a treatment which is effective in the treatment of anemias, more particularly the anemias of chronic disorders and of those conditions in which anemia may occur as a toxic side effect of treatment.

SUMMARY OF INVENTION

These and other objects of the present invention may be achieved by providing a method for the treatment of patients suffering from anemia which comprises orally administering to the patients effective doses of a serotonin antagonist, the administration taking place once a day every evening.

Although any serotonin antagonist can be used in the treatment according to the invention, cyproheptadine, which is sold under the trade mark, Periactin, is preferred because it is relatively inexpensive, readily available and has been demonstrated by us to have such therapeutic effects.

In accordance with a preferred embodiment of the invention, the administration takes place between 6 and about 10 o'clock p.m. and preferably as soon as possible after sunset.

In accordance with another preferred embodiment of the invention, the administration takes place with doses of about 0.5 to 4 mg of a serotonin antagonist, such as cyproheptadine.

Preferably, the serotonin antagonist is conditioned in a suspension or a tablet.

TEST TREATMENTS 150 patients with carcinoma cervix were clinically examined and staged as per the FIGO classification. Forty patients were awaiting treatment with surgery or $Co^{60}$ and were followed for 6 weeks as untreated controls (Group C). Another 50 patients, who were also awaiting treatment with surgery or $Co^{60}$, took 4 mg cyproheptadine orally in a single dose once daily soon after sundown. During the year that followed, all, except 8 of the 50 patients, had received either treatment with $Co^{60}$ or surgery. These 8 were patients who refused the radiation or surgical treatment. Of the remaining 42, 6 patients received surgery, that is, hysterectomy (Group PS), 13 received treatment with $Co^{60}$ at about the same time as they first began to take cyproheptadine (Group PR1), while another 23 received the same treatment some 4 months after going on cyproheptadine (Group PR2). Group PS also waited about 4 months before undergoing surgery. This time interval is not unusual under conditions where facilities are heavily taxed and the degree of compliance is relatively poor. Another 25 patients received surgery only (Group S) and another 35 received only treatment with $Co^{60}$ (Group R) which was applied to the pelvic region externally or as an intravaginal implant at intervals for 2 or 3 weeks as required.

As shown in the table, all the groups which were later to receive cyproheptadine had significantly lower hemoglobin levels before treatment with cyproheptadine than those who were not to be treated with cyproheptadine ($p < 0.02$). A year later, the situation was essentially the reverse. This was because in the interval the hemoglobin levels of the cyproheptadine-treated groups had increased significantly while those of the others had decreased, some significantly. Groups PR1, PR2 and PS also significantly increased their body weights soon after starting on cyproheptadine, an increase maintained for at least one year so far, while the patients in the non-cyproheptadine groups did not.

Clinical observation indicated that most of the cancer patients on cyproheptadine not only benefited from an increase in their hemoglobin level but in general enjoyed a distinctly better quality of life in terms of lesser morbidity and greater mobility. For example, many of the patients with cervical cancer were anemic, anoretic and cachetic before and even after treatment with $Co^{60}$ or surgery alone. Moreover, they generally restricted themselves to the confines of their homes where they experienced increasing difficulty in attending to household chores. On the other hand, most of those treated with cyproheptadine in addition to surgery or radiation were clearly less anemic, less morbid, more mobile, generally showed a lesser degree of lassitude and a lesser mortality after one year.

These effects could not have been due to vitamin or iron deficiency as all patients were issued supplements on their first visit. Indeed, it was because of the limited effect of vitamin and iron supplements that it was decided to introduce the use of cyproheptadine to these patients.

Because of the positive effects of using cyproheptadine in cancer patients treated with radiation or surgery, it is suggested that it also be used in those treated with drugs which may have toxic side effects. Patients with anemia due to chronic disease other than cancer such as those suffering from AIDS or those ill with chronic kidney disease and requiring dialysis are also suitable subjects for treatment with cyproheptadine. Anemia in kidney disease can be debilitating and life shortening and treatment with erythropoietin is currently being considered at about $5000 per annum per patient. Substituting cyproheptadine for erythropoietin would greatly reduce the cost.

Cyproheptadine has anti-serotonin properties and can cross the blood-brain barrier. Therefore, it can act both on the central nervous system, neuroendocrine axis and peripheral tissues. When given after sunset, cyproheptadine decreases nocturnal serotonin and in addition has other melatonin-like properties. That is, it acts like a melatonin agonist when given at night. Melatonin has been implicated in enhancing immunity, hematopoiesis and oncostatic effects. In addition, nocturnal melatonin has been reported to have profound effects on the hypothalamic-pituitary-adrenal-gonadal system, peripheral tissues, sleep and aging processes, whereas serotonin has been shown to have effects opposite to those of melatonin. This is the reason why it is proposed that treatment with cyproheptadine be carried out at night only.

Of course, even though tests were made with cyproheptadine because it is more readily available, the same results would be obtained with any serotonin antagonist, as all these compounds would act as a melatonin agonist.

| | Hemoglobin Levels (g/dl) in Patients with Cervical Cancer Treated with Cyproheptadine Alone or in Combination with Surgery or $Co^{60}$ | | | | | | |
|---|---|---|---|---|---|---|---|
| Time (weeks) | C N = 40 | P N = 8 | S N = 25 | PS N = 6 | R N = 35 | PR1 N = 13 | PR2 N = 23 |
| Start | 10.8 ± 0.2 | 7.2 ± 0.7 | 11.1 ± 0.3 | 8.8 ± 0.8 | 11.0 ± 0.3 | 8.1 ± 0.4 | 8.4 ± 0.4 |
| 6 | 8.4 ± 0.4 | 8.5 ± 0.8 | 9.8 ± 0.4 | 10.3 ± 0.7 | 8.5 ± 0.3 | 8.7 ± 0.3 | 10.1 ± 0.5 |
| 10 | — | 9.8 ± 1.0 | — | 11.4 ± 0.5 | — | 11.8 ± 0.4 | 11.3 ± 0.4 |
| 17 | — | 11.6 ± 0.6 | — | 11.8 ± 0.5 | — | 11.6 ± 0.4 | 11.2 ± 0.4 |
| 52 | — | 10.0 ± 0(2) | 9.8 ± 0.3(18) | 13.5 ± 0.4(6) | 10.4 ± 0.4(19) | 13.3 ± 0.5(10) | 11.7 ± 0.7(16) |

N = number of patients from "Start" to 17 weeks inclusive. At 52 weeks the number of patients is given in the brackets adjacent to the mean and standard error.
C = untreated controls; P = cyproheptadine alone; S = surgery alone; PS = cyproheptadine and surgery; R = $Co^{60}$ alone; PR1 = cyproheptadine and early $Co^{60}$; PR2 = cyproheptadine and later $Co^{60}$

We claim:

1. A method for the treatment of patients suffering from anemia, which comprises orally administering to said patients effective doses of cyproheptadene, said administration taking place once a day every evening.

2. A method according to claim 1, wherein said doses comprise about 0.5 to about 4 milligrams of said cyproheptadene.

3. A method according to claim 1, wherein said administration takes place between about 6 and about 10 o'clock p.m.

4. A method according to claim 3, wherein said administration takes place after sunset.

5. A method according to claim 1, for the treatment of anemia of chronic disorders.

6. A method according to claim 1, for the treatment of those anemias arising as side effects of the administration of therapeutic drugs.

7. A method according to claim 1, for the treatment of those anemias arising as side effects of the administration of ionizing radiation or kidney dialysis.

* * * * *